United States Patent [19]

Schu

[11] Patent Number: 5,916,237
[45] Date of Patent: Jun. 29, 1999

[54] POWER CONTROL APPARATUS AND METHOD FOR A BODY IMPLANTABLE MEDICAL DEVICE

[75] Inventor: Carl Schu, Brooklyn Park, Minn.

[73] Assignee: Medtronic, Inc., Minneapolis, Minn.

[21] Appl. No.: 09/070,265

[22] Filed: Apr. 30, 1998

[51] Int. Cl.⁶ .................................................. A61N 1/08
[52] U.S. Cl. .................................. 607/2; 607/16; 607/4; 600/522; 600/523
[58] Field of Search ..................... 607/4, 5, 2, 9, 607/16, 59, 39, 40, 42–46, 48, 50, 17; 600/509, 522, 523

[56] References Cited

U.S. PATENT DOCUMENTS

| | | | |
|---|---|---|---|
| 4,374,817 | 2/1983 | Lehman et al. | 423/319 |
| 4,379,459 | 4/1983 | Stein | 128/419 PG |
| 4,384,585 | 5/1983 | Zipes | 128/419 D |
| 4,548,209 | 10/1985 | Wielders et al. | 128/419 D |
| 4,556,063 | 12/1985 | Thompson et al. | 128/419 PT |
| 4,577,633 | 3/1986 | Berkovits et al. | 128/419 PG |
| 4,587,970 | 5/1986 | Holley et al. | 128/419 PG |
| 4,693,253 | 9/1987 | Adams | 128/419 D |
| 4,726,380 | 2/1988 | Vollmann et al. | 128/419 PG |
| 4,821,723 | 4/1989 | Baker, Jr. et al. | 128/419 D |
| 4,830,006 | 5/1989 | Haluska et al. | 128/419 PG |
| 4,880,005 | 11/1989 | Pless et al. | 128/419 PG |
| 4,949,719 | 8/1990 | Pless et al. | 128/419 D |
| 4,949,730 | 8/1990 | Cobben et al. | 128/775 |
| 5,022,395 | 6/1991 | Russie | 607/16 |
| 5,131,388 | 7/1992 | Pless et al. | 128/419 D |
| 5,144,949 | 9/1992 | Olson | 128/419 PG |
| 5,158,078 | 10/1992 | Bennett et al. | 128/419 PG |
| 5,199,428 | 4/1993 | Obel et al. | 128/419 C |
| 5,207,218 | 5/1993 | Carpentier et al. | 128/419 PG |
| 5,312,453 | 5/1994 | Shelton et al. | 607/19 |
| 5,314,430 | 5/1994 | Bardy | 607/5 |
| 5,330,507 | 7/1994 | Schwartz | 607/14 |
| 5,331,966 | 7/1994 | Bennett et al. | 128/696 |
| 5,354,316 | 10/1994 | Keimel | 607/15 |
| 5,447,519 | 9/1995 | Peterson | 607/5 |
| 5,545,186 | 8/1996 | Olson et al. | 607/14 |
| 5,573,003 | 11/1996 | Mann et al. | 607/16 |
| B1 4,830,006 | 10/1997 | Haluska et al. | 607/4 |

OTHER PUBLICATIONS

S. M. Sze, Bell Laboratories, Incorporated, Murray Hill, New Jersey, "Physics of Semiconductor Devices," Second Edition, a Wiley Interscience Publication, Copyright 1981 by John Wiley & Sons.

*Primary Examiner*—William E. Kamm
*Assistant Examiner*—Kennedy J. Schaetzle
*Attorney, Agent, or Firm*—Thomas F. Woods; Harold R. Patton

[57] ABSTRACT

An apparatus and method for controlling power in digital logic circuitry is disposed in a body implantable biomedical device disclosed. A power switch, such as a power gating transistor, is coupled to a digital logic circuit element to selectively control the application of power to the circuit element. During each system clock cycle, power is supplied to the circuit element only for a duration of time required to effect switching of logic states. Power is removed from the circuit element during each system clock cycle when no switching of logic states occurs. A clock signal applied to the gate of a power gating transistor selectively controls the supply of power to the digital circuit logic element during each system clock cycle so as to appreciably reduce static power consumption of the circuit element. The power control apparatus and method may be implemented in any digital logic design, and is well suited for use in digital circuitry that employs combinatorial logic of any complexity and any number of registers or latches. The appreciable reduction in static power consumption realized by employing the power control apparatus and method according to the present invention is particularly useful in digital logic circuitry applications designed to operate at relatively low switching frequencies and low power, such as implantable biomedical device applications.

38 Claims, 9 Drawing Sheets

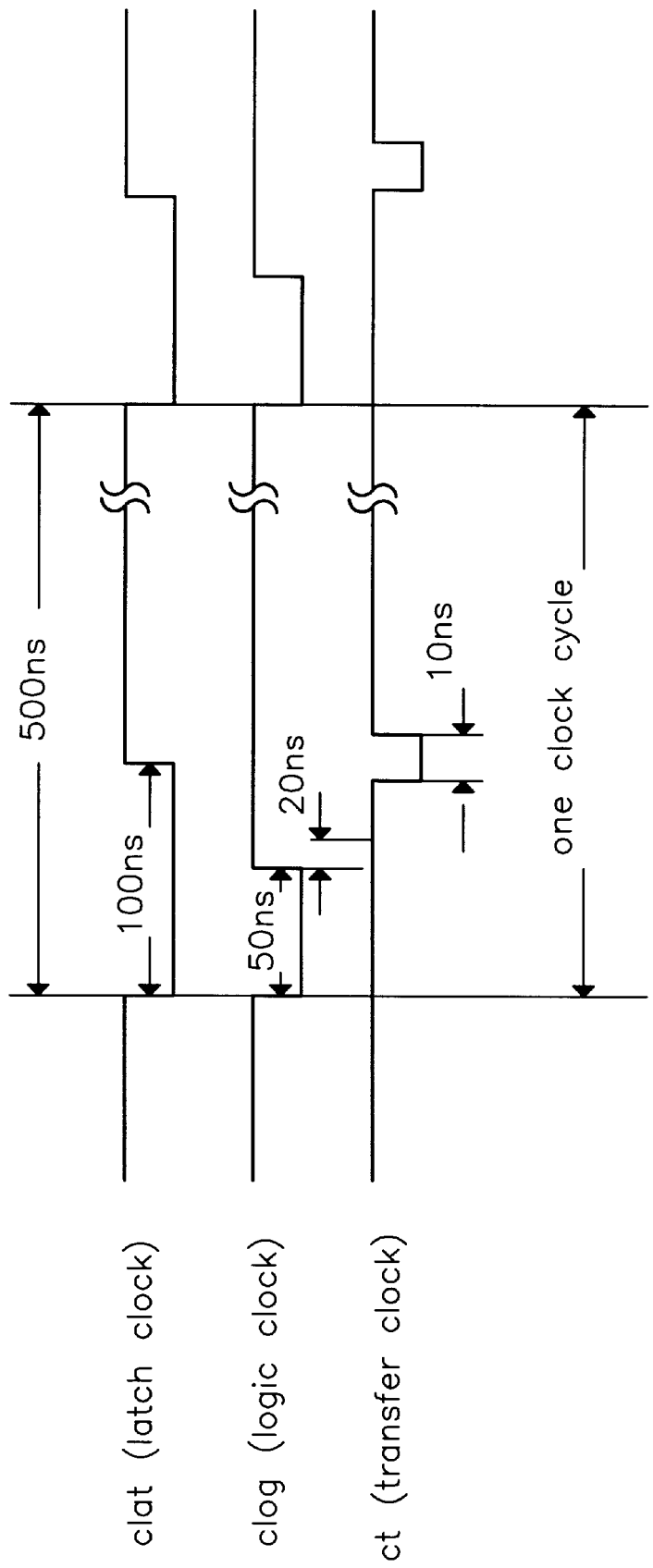

POWER CONTROL APPARATUS AND METHOD FOR A BODY IMPLANTABLE MEDICAL DEVICE

FIELD OF THE INVENTION

The present invention relates generally to a power control apparatus and method for controlling power supplied to digital logic circuitry. More particularly, the present invention pertains to an apparatus and method for minimizing power required to operate digital logic at relatively low switching frequencies, which is particularly useful when using such logic in low power, implantable medical device applications.

BACKGROUND OF THE INVENTION

Various techniques have been developed for fabricating semiconductor devices having small geometry features, such as on the order of 0.25 micron and below. Logic devices developed using small geometry fabrication processes often provide for low threshold voltages and reduced power consumption.

Increasing the speed at which a digital logic device transitions between logic states, commonly referred to as switching speed, has long been a primary motivation behind many advancements in the semiconductor arts. Increasing the switching speed of a logic device, however, results in a proportional increase of the power consumed by the device. The power consumed by a digital logic device while switching between logic states is commonly referred to as dynamic power consumption. As the demand for faster logic devices continues to increase, reducing the dynamic power consumption of logic devices continues to be of paramount importance in many high speed, low power applications.

Interestingly, dynamic power consumption is of less importance in applications where high switching speeds are not required or desired. In digital circuits that have relatively low switching frequencies, such as those typically employed in implantable medical devices, static power consumption becomes a predominate factor that, if left unaddressed, typically results in a dramatic increase in the overall level of power consumption. Static power consumption is understood in the art as power consumed by a device during periods in which no switching occurs. In some applications, static power consumption predominates over dynamic power consumption in the average power consumption equation.

The past and present focus by the semiconductor industry on reducing dynamic power consumption in high-speed digital logic devices has overshadowed the problems of increased static power consumption in digital devices and circuits designed to operate at low switching frequencies.

There is a need in the semiconductor manufacturing industry for an approach to reducing power consumption in digital logic devices and circuits intended for use in low switching frequency applications, such as implantable medical device applications. There is a further need for an approach that addresses problems associated with increased static power consumption in such digital logic devices and circuits. The present invention fulfills these and other needs.

SUMMARY OF THE INVENTION

The present invention has certain objects. That is, various embodiments of the present invention provide solutions to one or more problems existing in the prior art with respect to digital logic circuitry in general, and digital logic circuitry used in implantable medical devices in particular. Such problems include, for example, high power consumption and, in particular, high static power consumption, the present inability to selectively apply power and remove power to and from designated sections of digital logic circuitry without adversely affecting the functionality of the circuitry, and the present inability to exploit a low voltage threshold IC fabrication process that does not result in increased static power consumption for logic devices intended to operate at relatively low switching frequencies. Various embodiments of the present invention have the object of solving at least one of the foregoing problems. While some systems have been able to solve the general problem of reducing dynamic power consumption in digital logic devices and circuitry, such approaches have generally resulted in implementations that ignore the problem of increased static power consumption in low speed digital circuits. It is therefore another object of the present invention to provide an improved apparatus and methodology for controlling power to digital logic circuitry that fulfills at least one of the foregoing objects.

In comparison to known implementations of a power control scheme for digital logic circuitry, various embodiments of the present invention may provide one or more of the following advantages: reducing the average power consumption of digital logic circuitry; reducing the static power consumption of digital logic circuitry; reducing the size of digital circuitry while providing for the reduction of average power consumption and, in particular, static power consumption; and controlling the application and removal of power to and from selected portions of digital logic circuitry to reduce the average power and static power consumed by the circuitry.

Some embodiments of the invention include one or more of the following features: one or more power switches coupled to selected sections of digital circuitry to control the application of power to the selected circuitry sections; employing a power gating transistor responsive to clock signals to control the application of power to selected sections of digital logic circuitry; connecting a power gating transistor to a standard NAND gate, flip-flop, or other fundamental logic element for cycling power to such fundamental logic element; selectively applying and removing power to and from selected logic elements in complex logic circuitry during each system clock cycle without adversely affecting the operation of the logic circuitry; implementing, using a semiconductor fabrication process having a minimum geometry of less that 0.25 micron, one or more power switching transistors coupled to selected sections of digital circuitry to control the application of power to the selected circuitry sections; and implementing, using a semiconductor fabrication process having a minimum geometry on the order of 0.13 micron, one or more power switching transistors coupled to selected sections of digital circuitry to control the application of power to the selected circuitry sections.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 10 shows a timing diagram illustrating latch clock, logic clock, and transfer clock signals that control the selective application and removal of power to and from various circuit components of the circuitry in FIG. 5 or 8A when employing the modified NAND gate illustrated in FIG. 9.

Figure 1:
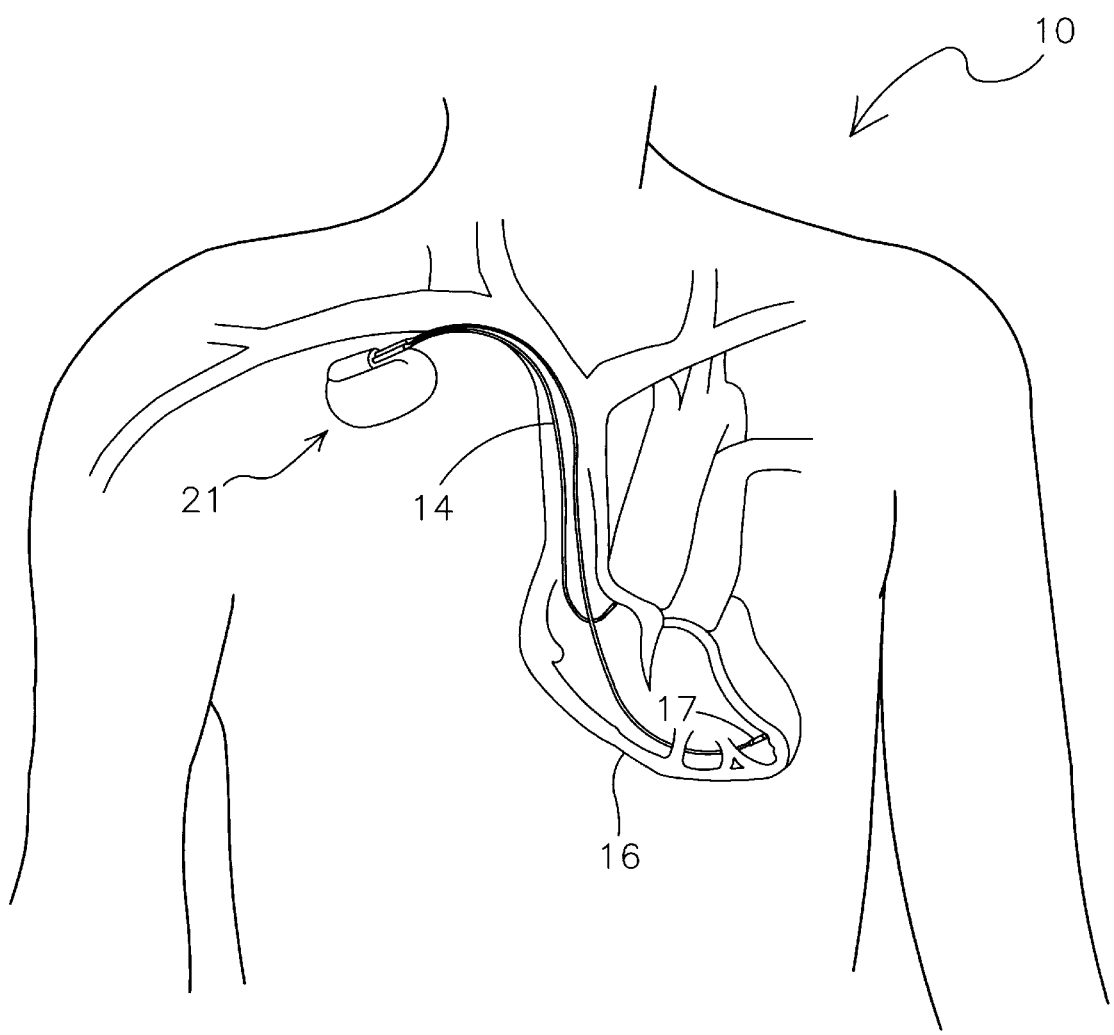
FIG. 1 shows an implantable medical device incorporating cycled power digital logic circuitry in accordance with an embodiment of the present invention implanted in a human body.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the spirit and scope of the invention as defined by the appended claims.

DETAILED DESCRIPTION OF THE EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

FIG. 1 is a simplified schematic view of a medical device 21 implanted in a human body 10. A cycled power logic apparatus and control methodology according to the present invention may be incorporated within the microprocessor based medical device 21 shown implanted in a human heart 16. It is to be understood that the cycled power logic methodology according to the present invention may by implemented in a wide variety of digital logic applications, including but not limited to medical device applications. Various objects and features of the present invention will be described herein generally within the context of combinatorial logic and latch/register circuitry. It is to be further understood that the principles of the present invention provide an approach to designing low power consuming digital logic of varying types and technologies, and that digital circuitry other than that described herein may be modified to incorporate the cycled power logic principles of the present invention.

In many implantable medical device applications, the speed at which a microprocessor based medical device operates is of secondary importance relative to size and power consumption considerations. The size of the components and circuitry incorporated in an implantable medical device, as well as the power requirements of such components and circuitry, are generally severely restricted.

Controlling the application and removal of power to one or more components of a digital logic circuit in a manner consistent with the principles of the present invention significantly decreases the overall power consumed by the digital circuitry. When implemented in medical device 21, the cycled power logic apparatus and methodology according to the present invention significantly reduces the power requirements of the medical device 21 and extends battery life. Further, employment of the cycled power logic apparatus and methodology according to the present invention provides the opportunity to exploit low power consuming digital devices, such as those fabricated using small geometry semiconductor processes, in the design of implantable medical devices. Additional reductions in power consumption may be realized by employing a cycled power logic approach according to the present invention in digital logic devices having submicron features, such as on the order of 0.13 micron.

It will be appreciated that a cycled power logic apparatus and methodology according to the present invention may be implemented in a wide variety of microprocessor based, implantable medical devices. In the case where the implanted medical device 21 shown in FIG. 1 is a pacemaker, one of the conductors of lead 14 is typically connected between the heart 16 and the implantable medical device 21. The medical device 21 typically includes a microprocessor, combinatorial logic, and register circuitry, all of which may incorporate cycled power logic circuitry according to the present invention, that cooperate to control the operation of the pacemaker,. The medical device 21 may be an implantable cardiac pacemaker, such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties.

The implantable medical device 21 may also be a pacemaker/cardioverter/defibrillator (PCD), one embodiment of which is further described below. The present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties. Those devices may be employed in conjunction with the cycled power logic methodology according to the present invention.

Alternatively, the medical device 21 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al., all of which are hereby incorporated herein by reference in their respective entireties. The present invention is believed to find wide application to any form of implantable electrical device which utilizes a microprocessor and ancillary digital circuitry, and the present invention is believed to be particularly advantageous in those contexts where a low power consumption design is employed or desired.

In general, the implantable medical device 21 shown in FIG. 1 includes a hermetically-sealed enclosure that may include various elements, such as an electrochemical cell (e.g., a lithium battery), circuitry that controls device operations and records arrhythmic EGM episodes, telemetry transceiver antenna and circuit that receives downlinked telemetry commands from and transmits stored data in a telemetry uplink to an external programmer, in addition to other elements.

Figure 2A:
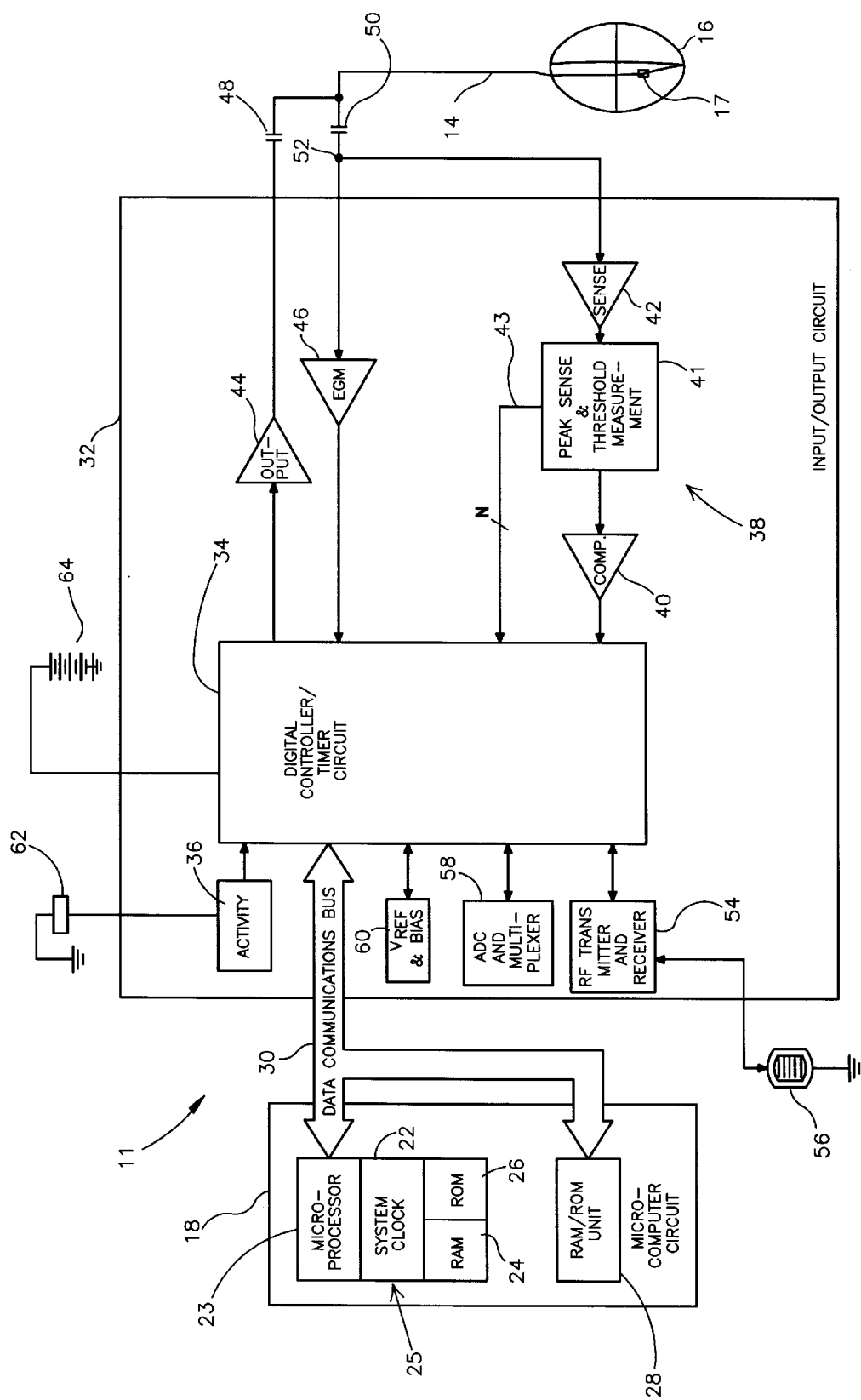
FIG. 2A shows an implantable pacemaker device incorporating cycled power digital logic circuitry in accordance with one embodiment of the present invention.

FIG. 2A is a block diagram illustrating various components of a pacemaker 11 which represents one of many implantable medical devices that may benefit from incorporating a cycle power logic approach in accordance with the principles of the present invention. In one embodiment, pacemaker 11 is programmable by means of an external programming unit (not shown). One such programmer suitable for the purposes of the present invention is the commercially available Medtronic Model 9790 programmer. The programmer is a microprocessor device which provides a series of encoded signals to pacemaker 11 by means of a programming head which transmits radio frequency (RF) encoded signals to pacemaker 11 according to a telemetry system such as that described in U.S. Pat. No. 5,312,453 to Wyborny et al., the disclosure of which is hereby incorporated by reference herein in its entirety. It is to be understood, however, that the programming methodology disclosed in the Wyborny et al. patent is identified herein for illustrative purposes only and that any programming methodology may be employed so long as the desired information is transmitted to and from the pacemaker 11. One of skill in the art may choose from any of a number of available programming techniques to accomplish this task.

Pacemaker 11, illustratively shown in FIG. 2A, is electrically coupled to the patient's heart 16 by lead 14. Lead 14, which includes two conductors, is coupled to a node 52 in the circuitry of pacemaker 11 through input capacitor 50. In the presently disclosed embodiment, an activity sensor 62 provides a sensor output to a processing/amplifying activity circuit 36 of input/output circuit 32. Input/output circuit 32 also contains circuits for interfacing with heart 16, antenna 56, and circuits 44 for application of stimulating pulses to heart 16 to moderate its rate under control of software-implemented algorithms in microcomputer unit 18.

Microcomputer unit 18 comprises on-board circuit 25 which includes microprocessor 20, system clock 22, and on-board RAM 24 and ROM 26. In this illustrative embodiment, off-board circuit 28 comprises a RAM/ROM unit. On-board circuit 25 and off-board circuit 28 are each coupled by a data communication bus 30 to digital controller/timer circuit 34.

The electrical components shown in FIG. 2A are powered by an appropriate implantable battery power source 64 in accordance with common practice in the art. For purposes of clarity, the coupling of battery power to the various components of pacemaker 11 is not shown in the figures.

Antenna 56 is connected to input/output circuit 32 to permit uplink/downlink telemetry through RF transmitter and receiver unit 54. Unit 54 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

Voltage reference ($V_{REF}$) and bias circuit 60 generates a stable voltage reference and bias current for the analog circuits of input/output circuit 32. Analog-to-digital converter (ADC) and multiplexer unit 58 digitizes analog signals and voltages to provide "real-time" telemetry intracardiac signals and battery end-of-life (EOL) replacement functions.

Operating commands for controlling the timing of pacemaker 11 are coupled by data bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sensing circuitry 38, including sense amplifier 42, peak sense and threshold measurement unit 41, and comparator/threshold detector 40.

Sense amplifier 42 amplifies sensed electrocardiac signals and provides an amplified signal to peak sense and threshold measurement circuitry 41. Circuitry 41, in turn, provides an indication of peak sensed voltages and measured sense amplifier threshold voltages on path 43 to digital controller/timer circuit 34. An amplified sense amplifier signal is then provided to comparator/threshold detector 40. Sense amplifier 42 may correspond to that disclosed in U.S. Pat. No. 4,379,459 to Stein, which is hereby incorporated by reference herein in its entirety.

Circuit 34 is further preferably coupled to electrogram (EGM) amplifier 46 for receiving amplified and processed signals sensed by an electrode disposed on lead 14. The electrogram signal provided by EGM amplifier 46 is employed when the implanted device is being interrogated by an external programmer (not shown) to transmit by uplink telemetry a representation of an analog electrogram of the patient's electrical heart activity. Such functionality is, for example, shown in previously referenced U.S. Pat. No. 4,556,063.

Output pulse generator 44 provides pacing stimuli to the patient's heart 16 through coupling capacitor 48 in response to a pacing trigger signal provided by digital controller/timer circuit 34. For example, each time the escape interval times out, an externally transmitted pacing command is received, or such commands are received in response to other stored commands as is well known in pacing art. Output amplifier 44, for example, may correspond generally to the output amplifier disclosed in U.S. Pat. No. 4,476,868 to Thompson, also incorporated by reference herein in its entirety.

Figure 2B:
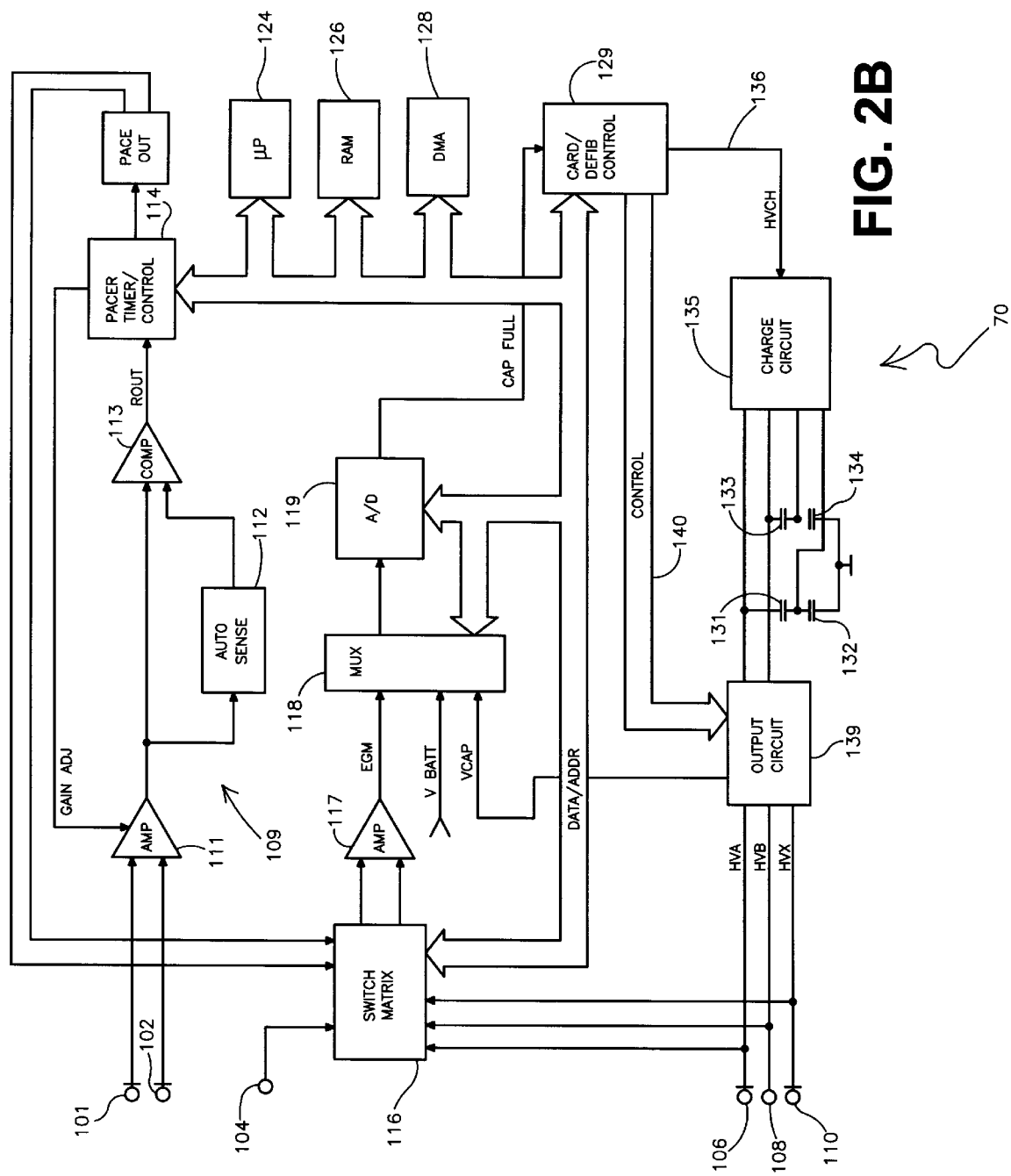
FIG. 2B shows one illustrative embodiment of a pacemaker/cardioverter/defibrillator unit incorporating cycled power digital logic circuitry in accordance with another embodiment of the present invention.

FIG. 2B is a functional schematic diagram from U.S. Pat. No. 5,447,519 to Peterson which shows an implantable pacemaker/cardioverter/defibrillator (PCD) 70 which represents another one of many implantable medical devices that may utilize a cycled power logic apparatus and methodology in accordance with the principles of the present invention. U.S. Pat. No. 5,447,519 is incorporated by reference herein in its entirety. It is understood that this diagram is an illustration of an exemplary type of device in which the invention may find application, and is not intended to limit the scope of the present invention.

Other implantable medical devices, such as those described previously, having functional organizations wherein the present invention may be useful, may also be modified to incorporate a cycled power logic apparatus and methodology in accordance with the present invention. For example, the present invention is also believed to be useful in conjunction with implantable pacemakers/cardioverters/ defibrillators as disclosed in U.S. Pat. No. 4,548,209 to Wielders, et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their respective entireties.

The PCD device 70 is provided with six electrodes 101, 102, 104, 106, 108, and 110. For example, electrodes 101 and 102 may be a pair of closely-spaced electrodes located in the ventricle. Electrode 104 may correspond to a remote, indifferent electrode located on the housing of the implantable PCD 70. Electrodes 106, 108, and 110 may correspond to large surface area defibrillation electrodes located on device leads or to epicardial electrodes.

Electrodes 101 and 102 are connected to detector circuit 109 which includes band pass filtered amplifier 111, auto-threshold circuit 112, which provides an adjustable sensing threshold, and comparator 113. A signal is generated by the comparator 113 whenever the signal sensed between electrodes 101 and 102 exceeds the sensing threshold defined by auto-threshold circuit 112. Further, the gain of amplifier 111 is adjusted by pacer timing and control circuitry 114. The sense signal, for example, is used to set the timing windows and to align successive waveshape data for morphology detection purposes. For example, the sense event signal may be routed through the pacer/timer control circuit 114 on data bus 115 to processor 124 and may act as an interrupt for processor 124 such that a particular routine of operations is commenced by processor 124.

Switch matrix 116 is used to select available electrodes under the control of processor 124 via data/address bus 115, such that the selection includes two electrodes employed as a far field electrode pair in conjunction with a tachycardia/ fibrillation discrimination function. Far field EGM signals from the selected electrodes are passed through band pass amplifier 117 and into multiplexer 118, where they are converted to multi-bit digital data signals by A/D converter 119 for storage in RAM 126 under the control of direct memory address circuitry 128.

The processor 124 may perform various morphology detection functions. For example, such detection functions may be indicative of tachycardia or fibrillation, or various other functions may be performed as set out in numerous references including any of the references incorporated herein by reference and others with regard to implantable PCDs.

The remainder of the device 70 of FIG. 2B is dedicated to the provision of cardiac pacing, cardioversion, and defibrillation therapies. The pacer timing/control circuit 114 includes programmable digital counters that control the basic timing intervals associated with cardiac pacing. Further, under control of processor 124, pacer timing/control circuit 114 also determines the amplitude of such cardiac pacing pulses.

In the event that a tachyarrhythmia is detected, and an anti-tachyarrhythmia pacing therapy is desired, appropriate timing intervals for controlling generation of pacing therapies are loaded from processor 124 into pacer timing and control circuitry 114. Similarly, in the event that generation of a cardioversion or defibrillation pulse is required, processor 124 employs the timing and control circuitry 114 to control timing of such cardioversion and defibrillation pulses.

In response to detection of fibrillation or a tachycardia requiring a cardioversion pulse, processor 124 activates cardioversion/defibrillation control circuitry 129, which initiates charging of the high voltage capacitors 131–134 via charging circuit 135 under the control of high voltage charging line 136. Thereafter, delivery and timing of the defibrillation or cardioversion pulse is controlled by pacer timing/control circuitry 114. One embodiment of an appropriate system for delivering and synchronizing cardioversion and defibrillation pulses, and controlling the timing functions related thereto, is disclosed in greater detail in U.S. Pat. No. 5,188,105 to Keimel, which is incorporated herein by reference in its entirety.

Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,374,817 to Engle et al., all of which are incorporated herein by reference in their respective entireties. Further, known circuitry for controlling the timing and generation of anti-tachycardia pacing pulses is described in U.S. Pat. No. 4,577,633 to Berkovitz et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their respective entireties.

Selection of a particular electrode configuration for delivery of the cardioversion or defibrillation pulses is controlled via output circuit 139 under the control of cardioversion/ defibrillation control circuit 129 via control bus 140. Output circuit 139 determines which of the high voltage electrodes 106, 108 and 110 is to be employed in delivering the defibrillation or cardioversion pulse regimen.

Figure 3:
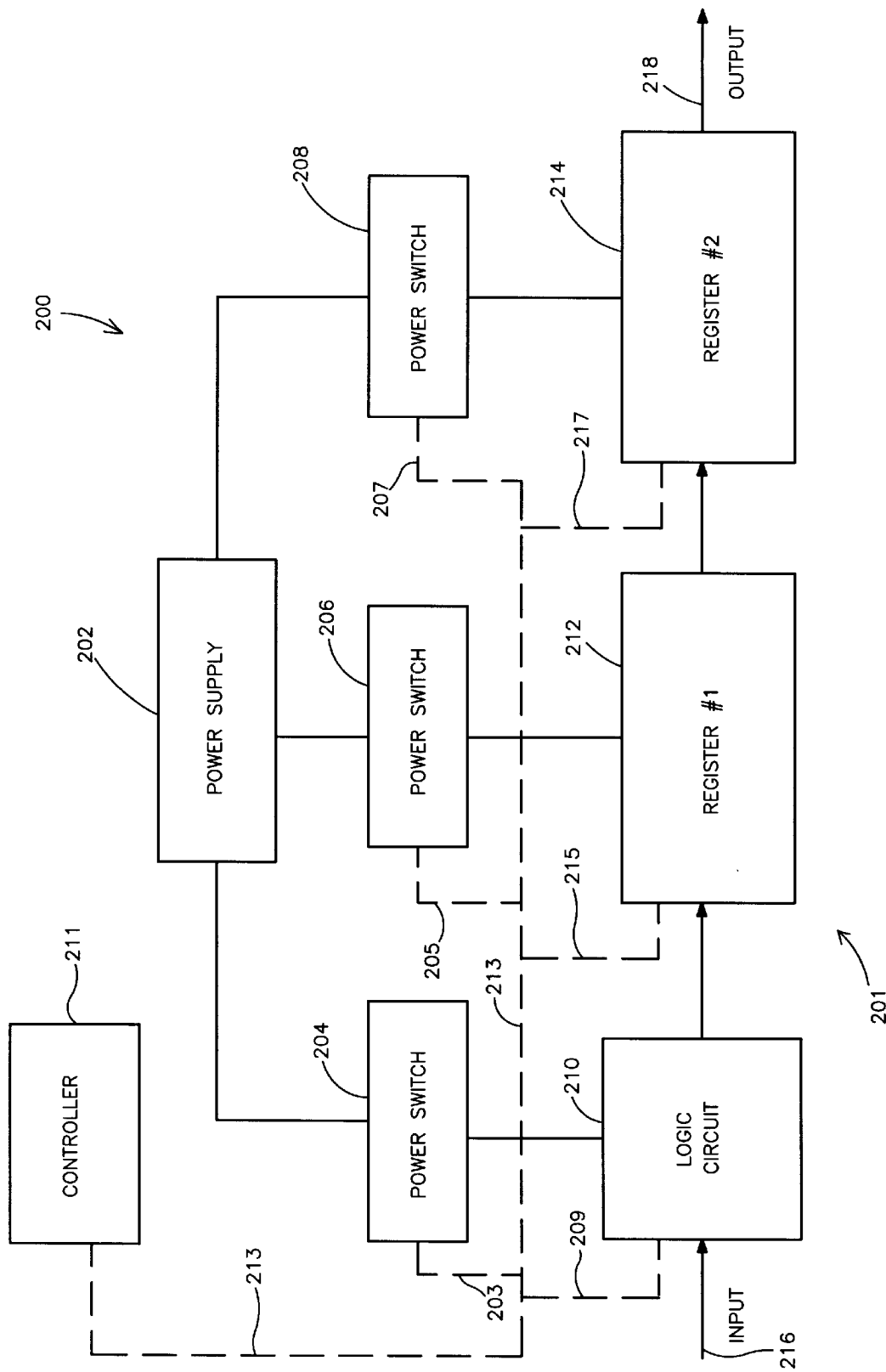
FIG. 3 shows an illustrative block diagram depicting circuitry for selectively applying and removing power to various digital circuit components in accordance with one embodiment of the present invention.

FIG. 3 shows a block diagram of an architecture for implementing a cycled power logic approach in accordance with one embodiment of the present invention. Many of the elements of circuitry 200 shown in FIG. 3 are intended to represent circuitry typically found in a wide variety of implantable medical devices. Significant power savings may be realized by integrating cycled power logic circuitry 200 according to the present invention within an implantable medical device, such as those described hereinabove and in the various patents incorporated herein by reference.

In low power applications, it is desirable to use electronic circuitry fabricated using small geometry semiconductor processes. Such small geometry devices provide for low threshold voltages that allow power supply voltages to be reduced. Lower supply voltages, in turn, provide for reduced power consumption, since power is proportional to the square of the voltage. This power advantage is realized during active switching, as the device transitions from one logic state to another. Power consumed by a device during logic state transitions is referred to as dynamic power consumption, and is characterized by the following equation:

$$P_{dyn} = V^2_{DD} f C \qquad [1]$$

where, $V_{DD}$ represents the supply voltage, f represents the switching frequency in hertz, and C represents the effective capacitance or power dissipation capacitance which includes the load capacitance. It can be seen from Equation [1] above that dynamic power consumption is directly proportional to the switching frequency of a device.

In circuits that have relatively low switching frequencies, such as those typically employed in implantable medical devices, the power consumed during times in which no switching occurs, referred to as static power consumption, becomes a predominate contributor to the average power consumed by the device. With regard to circuitry employed in many medical device applications and other circuits that have low clock frequencies, the average power consumed by low threshold voltage devices can be higher than that consumed by comparable high threshold voltage devices due to the impact of static power consumption. A cycled power logic design implemented in digital circuitry in accordance with the principles of the present invention is particularly advantageous when static power consumption becomes more pronounced.

In general, a cycled power logic design in accordance with the principles of the present invention may be implemented in any digital logic circuit, irrespective of the number of registers and complexity of combinatorial logic that may be implicated. In order to compensate for higher levels of static power consumption associated with low threshold voltage devices, the power delivered to selected sections of the digital logic circuitry is cycled between power ON and power OFF states. In many applications, most of the digital logic circuitry may be turned off at various times during each system clock cycle, which dramatically reduces static power consumption and average power consumption of the digital logic circuitry.

In the illustrative embodiment shown in FIG. 3, a digital circuit 201 of a conventional design is modified to include a number of power switches 204, 206, 208 that are controlled by a controller 211, which may be a microprocessor or other programmable control device. Power provided by power supply 202 is selectively applied to, and removed from, various circuit elements of digital circuit 201 in a coordinated manner by cooperation between controller 211 and power switches 204, 206, 208.

Digital circuit 201 includes logic circuit 210 and two registers, register #1 212 and register #2 214. Logic circuit 210 is intended to represent any type of digital logic, such as combinatorial logic. Registers #1 212 and #2 214 are intended to represent any type of circuit that may be used to store one or more bits of information, such as a latch, an addressable latch, or a memory device such as a RAM for example. In a conventional mode of operation, an input signal is presented at input 216 of logic circuit 210 and propagates through registers #1 212 and #2 214 by the application of appropriate clock signals to logic circuit 210, register #1 212, and register #2 214 in a manner known in the art. In accordance with a conventional approach, power would be provided on a continuous basis to logic circuit 210, register #1 212, and register #2 214 during normal operation.

In accordance with one embodiment of the present invention, power switches 204, 206, 208 are respectively coupled between logic circuit 210, register #1 212, and register #2 214 and power supply 202. Each of the power switches 204, 206, 208 is coupled to bus 213 of controller 211 by control lines 203, 205, 207, respectively. Controller 211 is also coupled to logic circuit 210, register #1 212, and register #2 214 by control lines 209, 215, 217, respectively. In response to control signals, typically clock signals, produced by controller 211, power switches 204, 206, 208 apply and remove power provided by power supply 202 to logic circuit 210, register #1 212, and register #2 214 so as to reduce the power consumed by digital circuit 200, yet not disrupt processing of data through digital circuit 200.

Figure 4:
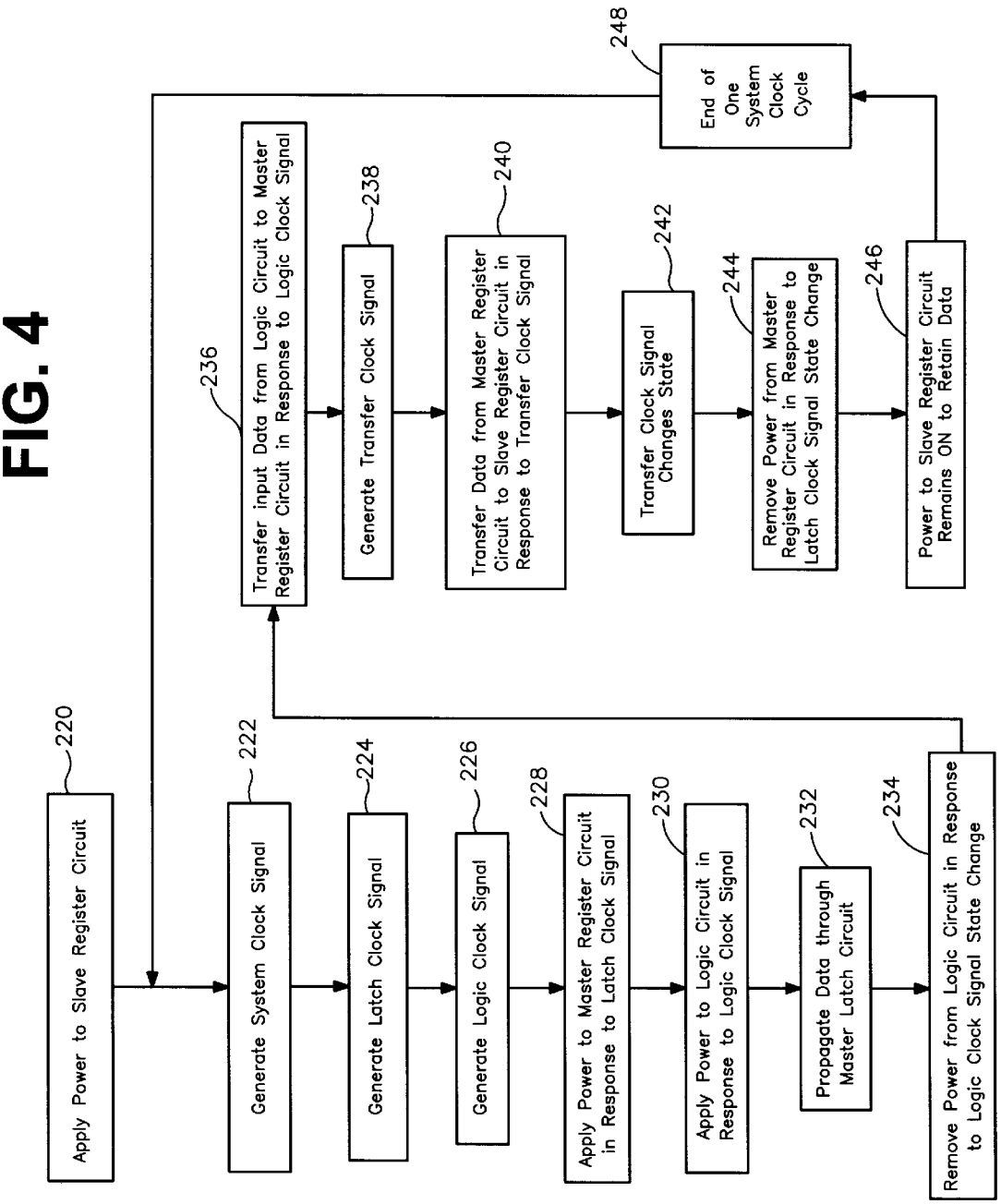
FIG. 4 shows in block diagram form various process steps involving the implementation of a power savings methodology for digital circuitry in accordance an embodiment of the present invention.
Figure 5:
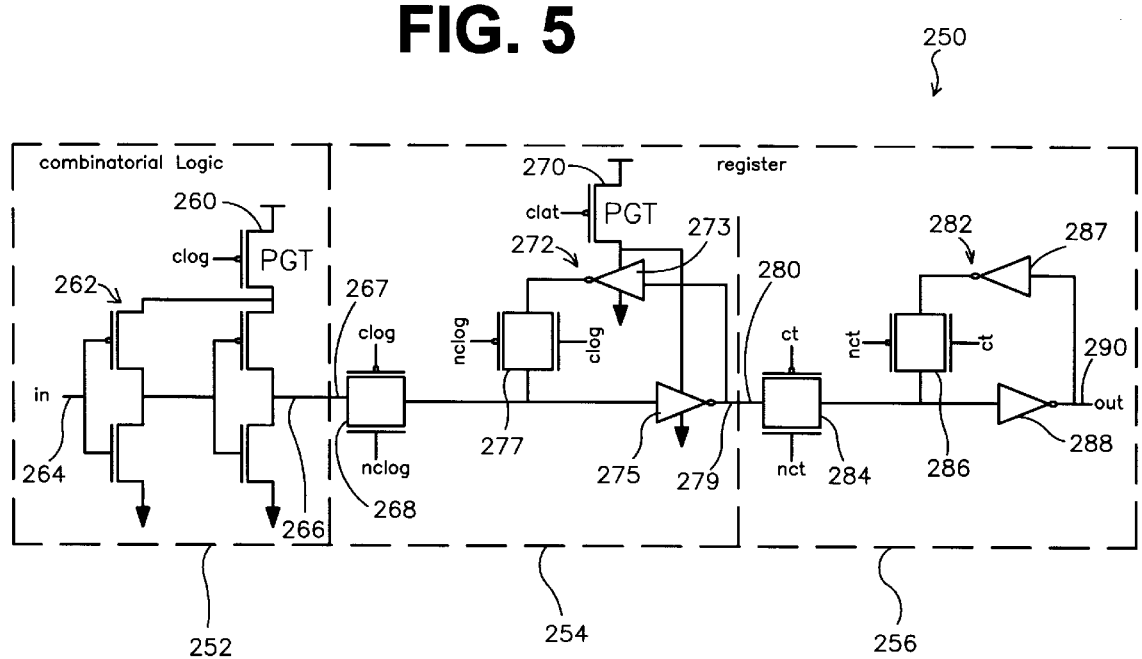
FIG. 5 shows a block diagram illustrating circuitry for selectively applying and removing power to various digital circuit components in accordance with another embodiment of the present invention.
Figure 6:
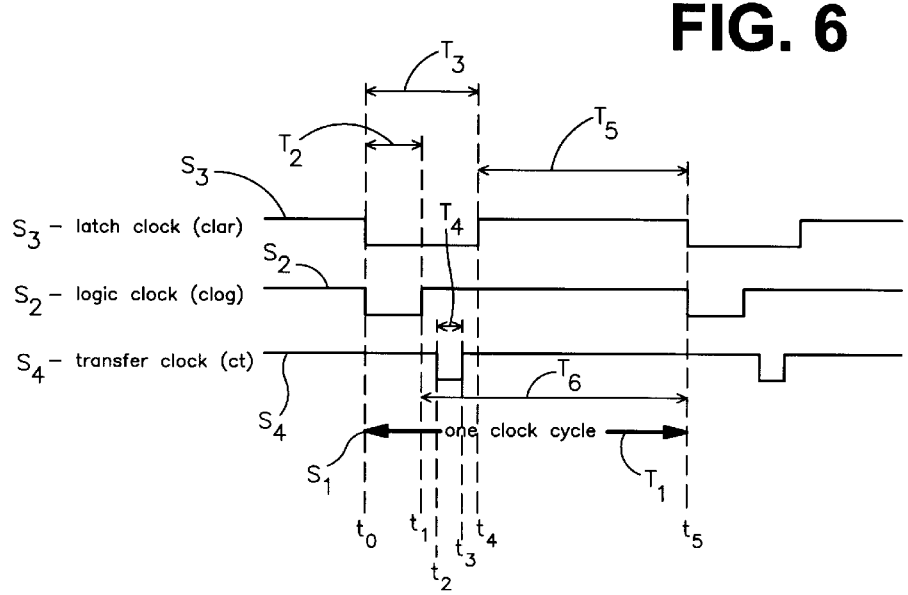
FIG. 6 shows a timing diagram illustrating latch clock, logic clock, and transfer clock signals that control the selective application and removal of power to and from various circuit components shown in FIG. 5.

Another embodiment of a digital circuit that incorporates cycled power logic circuitry according to the present invention is depicted in FIGS. 4 and 5. Digital circuit 250 includes combinatorial logic circuit 252, master register circuit 254, and slave register circuit 256. The timing diagram shown in FIG. 6 illustrates various clock signals applied to the digital circuit 250 to effectuate a cycled power logic methodology in accordance with one embodiment of the present invention. In general, during each system clock cycle of duration $T_1$, power is selectively applied to combinatorial logic circuit 252 and master register circuit 254 during only a portion of each system clock cycle. For example, and as shown in FIG. 6, power is applied to combinatorial logic circuit 252 during a portion $T_2$ of each system clock cycle of duration $T_1$. Power is also applied to master register circuit 254 during a portion $T_3$ of each system clock cycle. In the embodiment shown in FIGS. 4–6, power is applied to slave register circuit 256 on a continuous basis to ensure that the logic state at the output 290 of slave register circuit 256 is retained at the completion of each system clock cycle.

With power applied 220 to slave register circuit 256, a microprocessor or other timing control device, such as controller 211 shown in FIG. 3, generates 222 system clock signal $S_1$ at time $t_0$ having a duration $T_1$ during which the cycled power logic methodology according to the present invention is effectuated. Latch clock signal $S_3$, having a low logic level of duration $T_3$, is generated 224 at time $t_0$. Logic clock signal $S_2$, having a low logic level of duration $T_2$, is also generated 226 at time $t_0$. Application of latch clock signal $S_3$ to the gate of power gate transistor (PGT) 270 of master register circuit 254 at time $t_0$ causes transistor 270 to conduct so as to supply power 228 to master register circuit 254. Application of logic clock signal $S_2$ to the gate of power gate transistor 260 of combinatorial logic circuit 252 at time $t_0$ causes transistor 260 to conduct so as to supply power 230 to combinatorial logic circuit 252.

In this manner, power is supplied concurrently to combinatorial logic circuit 252 and master register circuit 254 at the beginning of each system clock cycle $T_1$. Combinatorial logic 262 is activated upon application of power to combinatorial logic circuit 252, such that a signal appearing at input 264 propagates 232 through combinatorial logic 262. An output signal produced by combinatorial logic 262 during time $T_2$ appears at output 266 which is coupled to input 267 of master register circuit 254. Latch 272 of master register circuit 254 is activated upon application of power to master logic circuit 254 in response to latch clock signal $S_3$ applied to the gate of transistor 270. Logic clock signal $S_2$ is applied to transmission gates 268 and 277 during time $T_2$ and time $T_3$ to control the propagation 232 of data through latch 272 to output 279 of master register circuit 254.

At time $t_1$, the state of logic clock signal $S_2$ transitions from a low logic level to a high logic level, causing transistor 260 of combinatorial logic circuit 252 to transition to a non-conducting state. As such, power is removed 234 from combinatorial logic circuit 252 at time $t_1$. Also, data present at the input 267 of master register circuit 254 is transferred 236 into latch 272 between time $t_1$ and time $t_4$. At time $t_2$, a transfer clock signal $S_4$ is generated 238 and applied to transmission gates 284 and 286 of slave register circuit 256. Data stored in latch 272 of master register circuit 254 is transferred to latch 282 of slave register circuit 256 on the rising edge of transfer clock signal $S_4$ at time $t_3$. At time $t_4$, power supplied through transistor 270 to master register circuit 254 is removed by a state change of latch clock signal $S_3$ from a low logic level to a high logic level.

The state of data presented at output 290 of slave register circuit 256 is retained by the continuous application of power to slave register circuit 256 during the remaining portion $T_5$ of the system clock cycle defined between time $t_4$ and $t_5$. It can be seen from FIG. 6 that no power is applied to combinatorial logic circuit 252 or master register circuit 254 during the portion $T_5$ of the system clock cycle defined between time $t_4$ and $t_5$. As will be discussed hereinbelow, the power saved by employment of a cycled power logic approach in accordance with the principles of the present invention is appreciable.

Figure 7A:
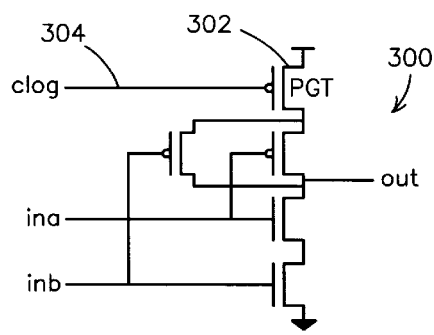
FIGS. 7A and 7B show a generic NAND gate schematic and a NAND gate in symbolic form, the NAND gates modified to implement a cycled power logic methodology in accordance with the principles of the present invention.
Figure 7B:
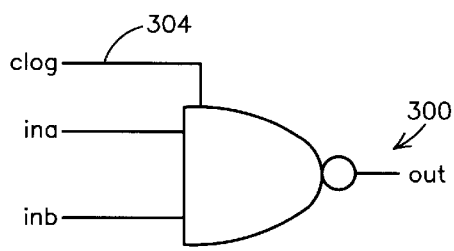

FIGS. 7A and 7B show schematic and symbolic illustrations of a NAND gate which is considered to be a fundamental logic unit by those skilled in the art. NAND gate 300 shown in FIGS. 7A and 7B is of a conventional configuration, with the exception that a power gate transistor 302 is coupled between the NAND gate and power supply (i.e., $V_{DD}$, not shown). Power transistor 302 is controlled by the logic level of logic clock signal 304 applied to the gate of the transistor 302. It is understood that the modified NAND gate 300 may be implemented in any digital logic design and appropriately controlled to advantageously reduce the static and average power consumption of the digital logic circuitry.

Figure 8A:
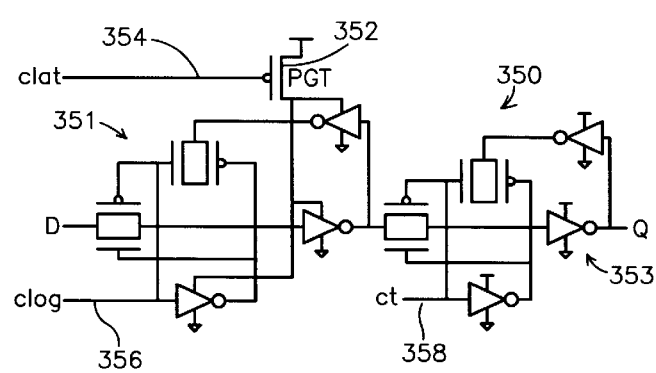
FIGS. 8A and 8B show a generic flip-flop schematic and a flip-flop in symbolic form, the flip-flops modified to implement a cycled power logic methodology in accordance with the principles of the present invention.
Figure 8B:
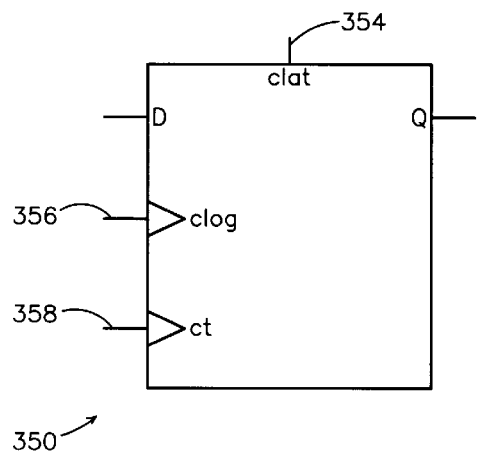

FIGS. 8A and 8B show schematic and symbolic illustrations of a flip-flop which is also considered to be a fundamental logic unit by those skilled in the art. The flip-flop 350 shown in FIGS. 8A and 8B may be characterized as a D flip-flop having a master-slave configuration, similar to that of the register circuits 254, 256 described previously with respect to FIG. 5. Flip-flop 300 shown in FIGS. 8A and 8B is of a conventional configuration, with the exception of power transistor 352 which is incorporated to control the application of power to the master circuit 351 of flip-flop 300. Transistor 352 is tied to the voltage supply node $V_{DD}$ (not shown) and transitions between conducting and non-conducting states in response to the logic state of latch clock signal 354 applied to the gate of transistor 352.

As with slave register circuit 256 of FIG. 5, power is continuously applied to slave circuit 353 during the entire system clock cycle. The operation of flip-flop 300 in response to latch clock signal 354, logic clock signal 356, and transfer clock signal 358 is similar to that described previously with respect to FIG. 5 as will be readily appreciated by one skilled in the art. It is to be understood that logic devices and circuitry other than NAND gates and flip-flops may be modified to include a power switching capability, such as by the incorporation of one or more power gate transistors, to implement a cycled power logic design in accordance with the principles of the present invention.

Figure 9:
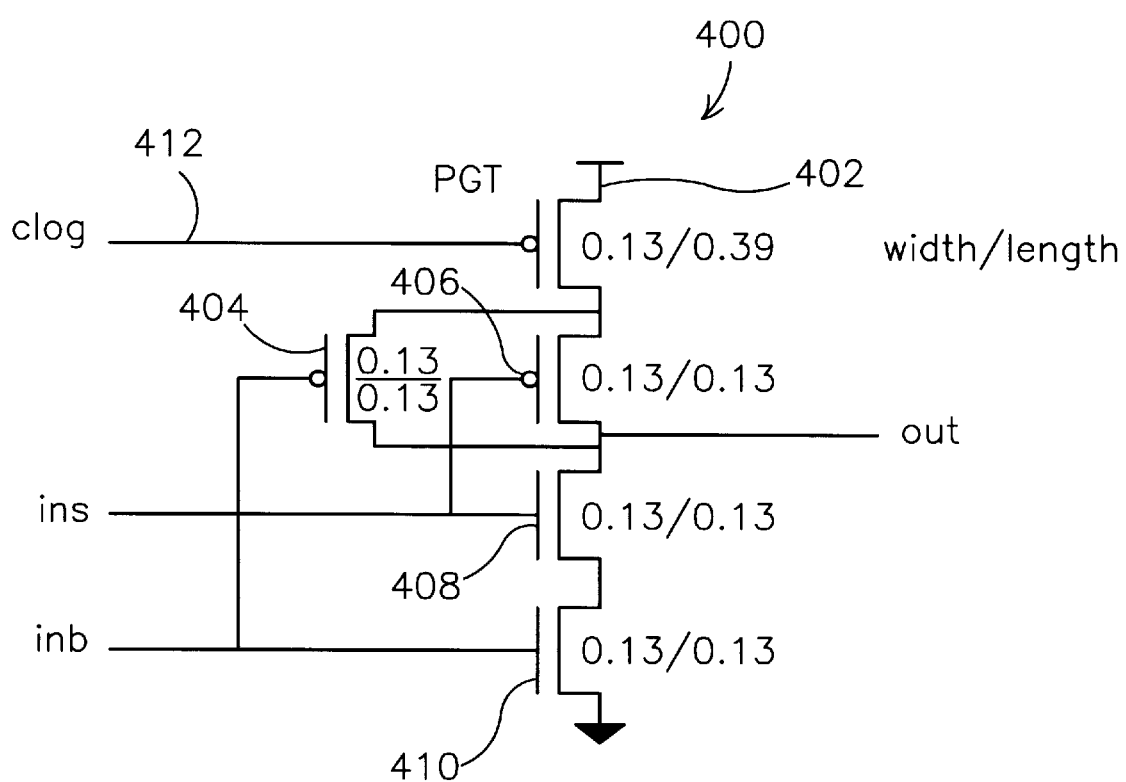
FIG. 9 shows a generic NAND gate schematic implemented as cycled power logic circuitry in accordance with an embodiment of the present invention.

FIG. 9 shows a schematic diagram of a digital circuit 400 configured as a NAND gate using low threshold voltage transistors. Digital circuit 400 also includes a power gating transistor 402 for purposes of implementing a cycled power logic design in accordance with the principles of the present invention. FIG. 10 is a timing diagram similar to that shown in FIG. 6 that characterizes the timing of the various clock signals applied to digital circuit 400. The following illustrative example demonstrates the dramatic power saving advantages realized when implementing a power switching approach according the present invention. For purposes of illustration, digital circuit 400 is assumed to be representative of digital circuitry typical of that employed in an implantable biomedical device. In particular, the following analysis has been developed based on typical pacing timing constraints associated with the operation of a pacemaker or PCD, such as the devices described previously with regard to FIGS. 2A and 2B.

For purposes of this analysis, digital circuit 400 is implemented in a 0.13 micron CMOS technology. In one embodiment, digital circuit 400 is employed in pacing timing circuitry to provide timing for the delivery of cardiac pacing pulses. It is assumed that the pacing timing circuit includes 3,000 gates of logic and operates at an average system clock frequency of 2 KHz. For purposes of estimating the size of the circuit 400, a "gate" is considered to constitute a 2-input NAND gate, the geometries of which are shown in FIG. 9. In particular, power gating transistor 402 has a channel length of 0.13 micron and a channel width of 0.39 micron. Transistors 404, 406, 408, and 410 each have a channel length of 0.13 micron and a channel width of 0.13 micron. The minimum geometry for the low threshold voltage process implicated in this illustrative example is assumed to be 0.13 micron.

The dynamic power consumption of the pacing timing circuit may be calculated using the following equations:

$$C_{tot} = 4LZC_i n_G r_f \qquad [2]$$

$$I_{dyn} = C_{tot} Vf \qquad [3]$$

where, L represents the channel length (0.13 micron), Z represents the channel width (0.13 micron), $C_i$ represents the oxide (insulator) capacitance ($1.38 \times 10^{-6}$ F/cm$^2$), $n_G$ represents the number of gates (3000), $r_f$ represents the route factor (3.5), $C_{tot}$ represents the total capacitance of the circuit, V represents the operating voltage (1.5 V), f represents the frequency of operation (2 KHz), and $I_{dyn}$ represents the dynamic current consumption (A). It is noted that the route factor, $r_f$, is an estimate of the amount of capacitance that will be added to the circuit when metal interconnect lines are added.

The dynamic current consumption, $I_{dyn}$, of the pacing timing circuit given the above conditions is 29 nA. Assuming that the pacing timing circuit is not implemented as a cycled power logic circuit (e.g., power gating transistors 402 are not present), the static current consumption of the pacing timing circuit may be calculated from the following formulas.

$$\phi_{ms} = \phi_m - \left(x + \frac{E_g}{2q} - \psi_B\right) \qquad [4]$$

$$V_{FB} = \phi_{ms} - \frac{Q_o}{C_i} \qquad [5]$$

$$\phi_{ms} = -\frac{E_g}{2q} - \psi_B \qquad [6]$$

where, Equation [6] assumes a poly-silicon gate, and a channel with p (acceptor) doping.

$$\beta = \frac{q}{kT} \qquad [7]$$

$$L_D = \sqrt{\frac{\varepsilon_s kT}{q^2 N_A}} \qquad [8]$$

$$a = \sqrt{2} \frac{\varepsilon_s}{\varepsilon_i} \frac{d}{L_D} \qquad [9]$$

$$\psi_B = \frac{kT}{q} \ln\left(\frac{N_A}{n_i}\right) \qquad [10]$$

$$C_i = \frac{\varepsilon_i}{d} \qquad [11]$$

$$V_T = V_{FB} + 2\psi_B + \frac{\sqrt{2\varepsilon_s q N_A (2\psi_B)}}{C_i} \qquad [12]$$

-continued $$V_{bi} = \frac{kT}{q} \ln\left(\frac{N_A N_D}{n_i^2}\right) \quad [13]$$

$$\psi_s = (V_G - V_{FB}) - \frac{a^2}{2\beta}\left\{\left[1 + \frac{4}{a^2}(\beta V_G - \beta V_{FB} - 1)\right]^{1/2} - 1\right\} \quad [14]$$

$$y_s = \sqrt{\frac{2\varepsilon_s}{qN_A}(V_{bi} - \psi_s)} \quad [15]$$

$$y_D = \sqrt{\frac{2\varepsilon_s}{qN_A}(V_{bi} - \psi_s + V_D)} \quad [16]$$

$$I_D = u_n\left(\frac{Z}{L - y_s - y_D}\right)\frac{aC_i}{2\beta^2}\left(\frac{n_i}{N_A}\right)^2(1 - e^{-\beta V_D})e^{\beta\psi_s}(\beta\psi_s)^{1/2} \quad [17]$$

$$I_{Dtot} = I_D n_G \quad [18]$$

where: k represents Boltzman's constant ($1.38066\times10^{-23}$ J/K); T represents temperature (300 K); q represents electron charge ($1.60281\times10^{-19}$ C); $\varepsilon_g$ represents the permittivity of Si ($1.053648\times10^{-12}$ F/cm); $\varepsilon_i$ represents the permittivity of $SiO_2$ ($3.453133\times10^{-13}$ F/cm); $\chi$ represents electron affinity (4.05 V for Si); $E_g$ represents the energy gap (1.12 eV for Si); $\phi_m$ represents the work function of metal (V); $\phi_{ms}$ represents the work function difference of metal to semiconductor (V); $\psi_B$ represents the potential difference between the Fermi level and the intrinsic Fermi level (V); $V_{FB}$ represents the flat band voltage (V); $V_T$ represents the threshold voltage (V); $V_{bi}$ represents the built in voltage (V); $V_G$ represents the gate voltage (V); $Q_o$ represents the oxide charge ($C/cm^2$); $C_i$ represents the insulator (gate) capacitance ($F/cm^2$); $L_D$ represents Debye length (cm); $N_D$ represents the donor impurity concentration ($1/cm^3$); $N_A$ represents the acceptor impurity concentration ($1/cm^3$); d represents the gate oxide thickness (cm); $n_i$ represents the intrinsic carrier concentration ($1cm^3$); $\psi_s$ represents surface potential (V); $y_s$ represents the channel depletion length at the source (cm); $Y_D$ represents the channel depletion length at the drain (cm); $V_D$ represents the drain to source voltage (V); $u_n$ represents electron mobility ($cm^2/V/s$); and $I_D$ represents the static current drain.

To calculate the static current drain, $I_D$, the following processing parameters are assumed for 0.13 micron geometries:

$N_A = 5.4\times10^{+17}$ ($1/cm^3$)
$N_D$(n source and drain)$=1.4\times10^{+17}$ ($1/cm^3$)
$t_{ox} = 25$ (Angstroms)
$u_n = 350$ ($cm^2$N/s)
$Q_o = 1\times10^{-10}$ ($C/cm^2$)
$V_t = 0.3$ (V)
$E_g/2q = 0.56$ (V) Given the above assumptions, $I_{Dtot}$ (static) is calculated to be 34 uA. This gives a ratio of static to dynamic current ($I_{Dtot}/I_{dyn}$) of about 1,200. For purposes of the additional power analysis provided below, the dynamic current may be ignored.

The gate delays of the pacing timing circuit may be estimated to be approximately 200 ps per gate. Since no delay path through the pacing timing circuit is longer than 50 gates, the longest delay path through the logic would be 10 ns. If the logic was slowed to one third of this speed, the longest delay path would be 30 ns. As such, the timing diagram shown in FIG. 10 represents a conservative implementation of the timing for the clocks used to drive the pacing timing circuit.

From the timing diagram provided in FIG. 10, it can be seen that almost all of the static power consumption occurs when latch clock signal, clat, is high (i.e., when the power gate transistors are OFF). Therefore, the power analysis continued below focuses on the case in which the power gate transistors are OFF.

From the schematic diagram of the NAND gate and the flip-flop shown in FIGS. 7A and 8A, it can be seen that the only part of the logic circuitry that is continuously powered (i.e., not connected to a power gating transistor) is the slave portion 353 of the flip-flop circuitry. Since there are approximately 200 flip-flops in the 3,000 gate pacing timing logic circuit, which represents a typical ratio of flip-flops to total logic for circuitry in a biomedical device, the circuitry that is continuously powered on will consume about ⅕ of the total current used in the pacing timing circuit, or about 7 uA.

The above estimation assumes that the slave portion of the flip-flop includes three inverters, each of which consumes about the same amount of static current as one gate of logic. Therefore, each flip-flop consumes the equivalent of 3 gates worth of static current, for a total of 600 gates worth of static current. This results in the ⅕ component (i.e., 600 gates/3, 000 gates) of the total current used by the pacing timing circuit. The remaining ⅘ of the current (i.e., about 27 uA) is consumed by circuitry that is switched by the power gating transistors. The amount of static current consumed in the PGT switched portion of the circuit will therefore be reduced to the amount of static current that flows through the PGTs (i.e., the leakage current when the PGTs are turned off).

PGT current consumption may be reduced by increasing the channel length of the transistor to something larger than the minimum geometry. In this case, the channel length of the PGT is increased to 0.39 micron, with the minimum geometry being 0.13 micron. Increasing the channel length in this manner slows down the logic that is switched by the PGT, since its own current is also decreased by increasing the channel length. This has been taken into account in the timing diagram provided in FIG. 10 by assuming an increase in gate delay of 3 times the previous delay without the PGT. Even if the gate delays are significantly increased, almost all of the current consumption will occur when the PGTs are turned off.

Calculating the static current drain of the PGT using this larger geometry (0.13 width/0.39 length) results in a static current drain that is ⅙ that of a minimum geometry (0.13 width/0.13 length) transistor. The current consumed by the PGT switched portion of the circuit is therefore reduced to ⅙ of what it would be without the PGTs (i.e. without implementing cycled power logic), which is 4.4 uA.

The total current consumption of the cycled power logic circuit is the sum of the current consumed by the logic not switched by the PGTs (i.e., 7 uA) plus the current consumed by the PGT switched logic (i.e., 4.5 uA), which is a total of 11.5 uA. This is about ⅓ the current consumed without the PGTs.

Additionally, if the gate lengths of the inverters in the slave portion of the flip-flop are increased only slightly, such as to a length of 0.17 microns for example, the static current consumed by this part of the circuit will be reduced to 4 uA, resulting in a total static current consumption of 8.5 uA. Therefore, by implementing cycled power logic, power consumption may be reduced to ¼ of what it would be with a standard logic implementation.

Those skilled in the art will appreciate that the channel length of the PGT may be altered relative to the channel lengths of the circuit transistors in the PGT switched portion of the digital circuitry to achieve a desired balance between switching speed, size (i.e., area), and static power consumption factors. In general, increasing the channel length of the PGT relative to the channel lengths of the other circuit transistors reduces static power consumption, but typically results in a decrease in switching speed and an increase in transistor area. Decreasing the channel length of the PGT relative to the channel lengths of the other circuit transistors increases the switching speed and decreases transistor area, but typically results in an increase in static power consumption. It will be further appreciated by one skilled in the art that the channel width of the PGT may be varied to accommodate varying power delivery requirements.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to use in conjunction with a particular type of digital logic device, such as a NAND gate or flip-flop, but may be used in conjunction with digital logic circuitry of varying configurations, functionality, and technologies. Further, the present invention may be employed in a wide variety of controller-based or processor-based system, such as implantable medical devices, and may further be implemented in low power applications other than in implantable medical devices. The present invention is also not limited to specific timing and control techniques, such as those presented herein, but such functions may be directed using other like techniques. The present invention further includes within its scope methods of using the cycled power logic apparatus according to the present invention as well as the structural particulars described hereinabove.

In the claims, means plus function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A body implantable medical apparatus, comprising:
a hermetically sealed housing;
a physiologic transducer coupled to a lead; and
a microprocessor disposed in the housing, the microprocessor coupled to the lead and digital circuitry for controlling operations of the implantable medical apparatus in response to signals generated by the transducer; the digital circuitry coupled to a power source and a control clock that produces a control clock signal during a period of each cycle of a series of system clock cycles, and the digital circuitry comprising:
a first register circuit;
a second register circuit coupled to the first circuit and receiving power from the power source continuously during each system clock cycle; and
a power switch coupled to the first register circuit and providing power to the first register circuit for a portion of time in response to a first state of the control clock signal, the first register circuit transferring data stored therein to the second register circuit in response to the first state of the control clock signal and the power switch removing power from the first register in response to a second state of the control clock signal;
whereby power is provided to the first register circuit only during the portion of time during each system clock cycle so as to reduce static power consumption of the digital circuitry.

2. The apparatus of claim 1, wherein each of the first and second register circuits comprises one or more transistors and the power switch comprises a power transistor, each of the transistors having a channel length approximately equal to a minimum channel length defined for a particular semiconductor fabrication process, and the power transistor having a channel length that exceeds the minimum channel length defined for the particular semiconductor fabrication process.

3. The apparatus of claim 1, wherein each of the first and second register circuits comprises one or more transistors and the power switch comprises a power transistor, each of the transistors having a channel length approximately equal to a minimum channel length defined for a particular semiconductor fabrication process, and the power transistor having a channel length that exceeds the minimum channel length defined for the particular semiconductor fabrication process by a factor of at least two.

4. The apparatus of claim 1, wherein each of the first and second register circuits comprises one or more transistors and the power switch comprises a power transistor, each of the transistors having a channel length approximately equal to a minimum channel length defined for a particular semiconductor fabrication process, and the power transistor having a channel length that exceeds the minimum channel length defined for the particular semiconductor fabrication process by a factor ranging between approximately one and three.

5. The apparatus of claim 1, wherein each of the first and second register circuits comprises one or more transistors and the power switch comprises a power transistor, each of the transistors having a channel length of less than approximately 0.15 micron, and the power transistor having a channel length of greater than approximately 0.2 micron.

6. The apparatus of claim 1, wherein each of the first and second register circuits comprises one or more transistors and the power switch comprises a power transistor, each of the transistors having a channel length of less than approximately 0.2 micron and the power transistor having a channel length of greater than approximately 0.3 micron.

7. The apparatus of claim 1, wherein the portion of time defines a duration of time one or more magnitudes less than the period of the system clock cycle.

8. The apparatus of claim 1, wherein the portion of time is on the order of nanoseconds, and the period of the system clock cycle is on the order of microseconds.

9. The apparatus of claim 1, wherein the digital circuitry is implemented within the microprocessor.

10. The apparatus of claim 1, wherein the power switch comprises a power gating transistor.

11. The apparatus of claim 1, wherein each of the first and second register circuits comprises one or more transistors and the power switch comprises a power transistor.

12. The apparatus of claim 1, wherein the body implantable medical apparatus is selected from the group consisting of a cardiac pacemaker, pacemaker/cardioverter/defibrillator, nerve stimulator, muscle stimulator, and implantable biomedical monitoring device.

13. A body implantable medical apparatus, comprising:
a hermetically sealed housing;
a physiologic transducer coupled to a lead;
a microprocessor disposed in the housing, the microprocessor coupled to the lead and digital circuitry for controlling operations of the implantable medical apparatus in response to signals generated by the transducer;

the digital circuitry coupled to a power source, a transfer clock, a logic clock, and a latch clock, the transfer clock, logic clock, and latch clock respectively producing a transfer clock signal, latch clock signal, and logic clock signal during each cycle of a series of system clock cycles, and the digital circuitry comprising;

a combinatorial logic circuit;

a first register circuit coupled to the combinatorial logic circuit;

a second register circuit coupled to the first circuit and receiving power from the power source continuously during each system clock cycle;

a first power switch coupled to the combinatorial logic circuit and providing power to the combinatorial logic circuit for a first portion of time in response to a first state of the logic clock signal, the combinatorial logic circuit transferring data to the first register circuit and the first power switch removing power from the combinatorial logic circuit in response to a second state of the logic clock signal; and a second power switch coupled to the first register circuit and providing power to the first register circuit for a second portion of time in response to a first state of the latch clock signal, the first register circuit transferring data to the second register circuit in response to a state change of the transfer clock signal and the second power switch removing power from the first register circuit in response to a second state of the latch clock signal;

whereby power is provided to the combinatorial logic circuit and the first register circuit only during respective first and second portions of time during each system clock cycle so as to reduce static power consumption of the digital circuitry.

14. The apparatus of claim 13, wherein each of the combinatorial circuit, first register circuit, and second register circuit comprises one or more transistors, and each of the first and second power switches comprises a power transistor, each of the transistors having a channel length approximately equal to a minimum channel length defined for a particular semiconductor fabrication process, and each of the power transistors having a channel length that exceeds the minimum channel length defined for the particular semiconductor fabrication process.

15. The apparatus of claim 13, wherein each of the combinatorial circuit, first register circuit, and second register circuit comprises one or more transistors, and each of the first and second power switches comprises a power transistor, each of the transistors having a channel length approximately equal to a minimum channel length defined for a particular semiconductor fabrication process, and each of the power transistors having a channel length that exceeds the minimum channel length defined for the particular semiconductor fabrication process by a factor ranging between approximately one and three.

16. The apparatus of claim 13, wherein each of the combinatorial circuit, first register circuit, and second register circuit comprises one or more transistors, and each of the first and second power switches comprises a power transistor, each of the transistors having a channel length of less than approximately 0.15 micron, and each of the power transistors having a channel length of greater than approximately 0.2 micron.

17. The apparatus of claim 13, wherein each of the first and second time portions defines duration of time one or more magnitudes less than the period of the system clock cycle.

18. The apparatus of claim 13, wherein each of the first and second time portions is on the order of nanoseconds, and the period of the system clock cycle is on the order of microseconds.

19. The apparatus of claim 13, wherein the first time portion is longer in duration than the second time portion.

20. The apparatus of claim 13, wherein each of the first and second power switches comprises a power gating transistor.

21. The apparatus of claim 13, wherein each of the combinatorial circuit, first register circuit, and second register circuit comprises one or more transistors, and each of the first and second power switches comprises a power transistor.

22. The apparatus of claim 13, wherein each of the combinatorial circuit, first register circuit, and second register circuit comprises one or more transistors, and each of the first and second power switches comprises a power transistor, each of the transistors having a channel length of less than approximately 0.2 micron and each of the power transistors having a channel length of greater than approximately 0.3 micron.

23. The apparatus of claim 13, wherein each of the first and second time portions defines a duration of time less than half of the period of the system clock cycle.

24. The apparatus of claim 13, wherein the first time portion ranges between 100 nanoseconds and 1 microsecond, the second time portion ranges between 50 nanoseconds and 1 microsecond, and the period of the system clock cycle exceeds 100 microseconds.

25. The apparatus of claim 13, wherein the body implantable medical apparatus is selected from the group consisting of a cardiac pacemaker, pacemaker/cardioverter/defibrillator, nerve stimulator, muscle stimulator, and implantable biomedical monitoring device.

26. A method of controlling power provided to digital circuitry disposed in a body implantable medical device, the method comprising:

providing in the body implantable medical device a first register circuit and a second register circuit;

generating system clock signals, each of the system clock signals defining a cycle having an associated period;

providing power to the second register circuit continuously during each system clock cycle;

providing power to the first register circuit and transferring data from the first register circuit to the second register circuit within a portion of time during each system clock cycle, the time portion defining a duration of time less than the period of the system clock cycle; and removing power from the first register circuit after transferring data from the first register circuit to the second register circuit, whereby power is provided to the first register circuit only during the portion of time during each system clock cycle so as to reduce static power consumption of the digital circuitry disposed in the body implantable medical device.

27. The method of claim 26, wherein:

generating system clock signals comprises generating system clock signals each having a period on the order of microseconds; and the time portion defines a duration of time on the order of nanoseconds.

28. The method of claim 26, wherein:

generating system clock signals comprises generating system clock signals each having a period of greater than 100 microseconds; and the time portion defines a duration of time ranging between 10 nanoseconds and 1 microsecond.

29. The method of claim 26, wherein:

generating system clock signals comprises generating system clock signals each having a period of greater than 1 microsecond; and the time portion defines a duration of time ranging between 10 nanoseconds and 500 nanoseconds.

30. The method of claim 26, wherein the time portion defines a duration of time one or more magnitudes less than the period of the system clock cycle.

31. A method of controlling power provided to digital circuitry disposed in a body implantable medical device, the method comprising:

providing in the body implantable medical device a combinatorial logic circuit and register circuitry, the register circuitry including a master register circuit and a slave register circuit;

generating a system clock signal;

generating, during each cycle of the system clock signal, a latch clock signal, a logic clock signal, and a transfer clock signal;

providing power to the slave register circuit continuously during each system clock cycle;

providing power to the combinatorial logic circuit and propagating data through the combinatorial logic circuit in response to the logic clock signal;

providing power to the master register circuit in response to the latch clock signal;

transferring the data from the combinatorial logic circuit to the master register circuit and then removing power from the combinatorial logic circuit in response to a state change of the logic clock signal;

transferring data from the master register circuit to the slave register circuit in response to the transfer clock signal; and removing power from the master register circuit in response to a state change of the latch clock signal;

whereby power is provided to the combinatorial logic circuit and the master register circuit only during a respective first and second time portion of each system clock cycle so as to reduce static power consumption of the digital circuitry disposed in the body implantable medical device.

32. The method of claim 31, wherein:

generating system clock signals comprises generating system clock signals each having a period on the order of microseconds; and each of the first and second time portions defines a duration of time on the order of nanoseconds.

33. The method of claim 31, wherein each of the first and second time portions defines a duration of time one or more magnitudes less than the period of the system clock cycle.

34. A body implantable medical apparatus, comprising:

a hermetically sealed housing;

a first register circuit coupled to a second register circuit, the first and second register circuits disposed in the hermetically sealed housing;

means for generating system clock signals, each of the system clock signals defining a cycle having an associated period;

means for providing power to the second register circuit continuously during each system clock cycle;

means for providing power to the first register circuit and transferring data from the first register circuit to the second register circuit within a portion of time during each system clock cycle, the time portion defining a duration of time less than the period of the system clock cycle; and means for removing power from the first register circuit after transferring data from the first register circuit to the second register circuit;

whereby power is provided to the first register circuit only during the portion of time during each system clock cycle so as to reduce static power consumption of circuitry disposed in the body implantable medical apparatus.

35. The apparatus of claim 34, wherein:

the generating means comprises means for generating system clock signals each having a period on the order of microseconds; and the time portion defines a duration of time on the order of nanoseconds.

36. The apparatus of claim 34, wherein:

the generating means comprises means for generating system clock signals each having a period of greater than 1 microsecond; and the time portion defines a duration of time ranging between 10 nanoseconds and 500 nanoseconds.

37. The apparatus of claim 34, wherein the time portion defines a duration of time one or more magnitudes less than the period of the system clock cycle.

38. The apparatus of claim 34, wherein the body implantable medical apparatus is selected from the group consisting of a cardiac pacemaker, pacemaker/cardioverter/defibrillator, nerve stimulator, muscle stimulator, and implantable biomedical monitoring device.

* * * * *